(12) United States Patent
Sheard et al.

(10) Patent No.: US 8,106,138 B2
(45) Date of Patent: Jan. 31, 2012

(54) RANDOM PROPYLENE COPOLYMER COMPOSITIONS, ARTICLES AND PROCESS

(75) Inventors: William G. Sheard, Houston, TX (US); Linfeng Chen, Sugar Land, TX (US); Daniel W. Baugh, III, Lake Jackson, TX (US); Peter S. Martin, Houston, TX (US)

(73) Assignee: Dow Global Technologies LLC, Midland, MI (US)

( * ) Notice: Subject to any disclaimer, the term of this patent is extended or adjusted under 35 U.S.C. 154(b) by 214 days.

(21) Appl. No.: 12/650,633

(22) Filed: Dec. 31, 2009

(65) Prior Publication Data

US 2010/0197874 A1 Aug. 5, 2010

Related U.S. Application Data

(60) Provisional application No. 61/141,902, filed on Dec. 31, 2008, provisional application No. 61/141,959, filed on Dec. 31, 2008.

(51) Int. Cl.
*C08F 210/02* (2006.01)
*C08F 210/06* (2006.01)
*C08F 2/00* (2006.01)
*C08F 210/00* (2006.01)

(52) U.S. Cl. .......................... 526/213; 526/348; 526/89

(58) Field of Classification Search .................. 526/89, 526/213, 348
See application file for complete search history.

(56) References Cited

U.S. PATENT DOCUMENTS

2005/0119427 A1* 6/2005 Wei et al. .................. 526/125.3

FOREIGN PATENT DOCUMENTS

| WO | 03/068828 A1 | 8/2003 |
|---|---|---|
| WO | 2006/065799 A2 | 6/2006 |
| WO | 2006/120190 A1 | 11/2006 |
| WO | 2007/045600 A1 | 4/2007 |
| WO | 2008/000515 A1 | 1/2008 |

OTHER PUBLICATIONS

E.P. Otocka et al., Macromolecules, 4, 507-514 (1971).
Th.G. Scholte et al., J. Appl. Polym. Sci., 29, 3763-3782 (1984).

* cited by examiner

*Primary Examiner* — William Cheung
(74) *Attorney, Agent, or Firm* — Whyte Hirschboeck Dudek SC

(57) ABSTRACT

The present disclosure is directed to random propylene/α-olefin compositions, articles, and processes for producing the same. The present compositions contain a random copolymer of propylene and α-olefin. Polymerization with an improved catalyst composition increases the molecular weight distribution of the copolymer and increases the randomness of comonomer distribution to yield random propylene/α-olefin copolymers with improved stiffness and/or improved optical properties.

3 Claims, No Drawings

US 8,106,138 B2

RANDOM PROPYLENE COPOLYMER COMPOSITIONS, ARTICLES AND PROCESS

PRIORITY CLAIM

This application claims priority to U.S. provisional patent application Ser. No. 61/141,902 filed on Dec. 31, 2008, and U.S. provisional patent application Ser. No. 61/141,959 filed on Dec. 31, 2008, the entire content of each application incorporated by reference herein.

BACKGROUND

The present disclosure relates to compositions and articles containing a random propylene/α-olefin copolymer and processes for producing the same. The propylene/α-olefin copolymer includes a substituted phenylene aromatic diester.

Worldwide demand for olefin-based polymers continues to grow as applications for these polymers become more diverse and more sophisticated. Known are Ziegler-Natta catalyst compositions for the production of olefin-based polymers and propylene-based compositions in particular. Ziegler-Natta catalyst compositions typically include a procatalyst containing a transition metal halide (i.e., titanium, chromium, vanadium), a cocatalyst such as an organoaluminum compound, and optionally an external electron donor. Ziegler-Natta catalyzed propylene-based polymers typically exhibit a narrow range of molecular weight distribution. Given the perennial emergence of new applications for propylene-based polymers, the art recognizes the need for propylene-based polymers with improved and varied properties. Desirable would be propylene-based compositions with improved properties such improved stiffness and/or improved optical properties.

SUMMARY

The present disclosure is directed to propylene/α-olefin compositions, articles thereof, and processes for producing the same. The present compositions are produced from a catalyst composition that contains a substituted phenylene aromatic diester which subsequently increases the random distribution of the comonomer within the formant polymer chain. The increased comonomer randomness resulting from the substituted phenylene aromatic diester yields random propylene/α-olefin copolymers with improved stiffness and/or improved optical properties.

The present disclosure provides a process. In an embodiment, a polymerization process is provided and includes contacting, under polymerization conditions, propylene and ethylene with a catalyst composition comprising a substituted phenylene aromatic diester, and forming a random propylene/ethylene copolymer with a Koening B-value from about 0.83 to about 1.0.

The present disclosure provides a composition. In an embodiment, a composition is provided and includes a random propylene/ethylene copolymer. The composition also includes a substituted phenylene aromatic diester.

In an embodiment, the composition has a Koening B-value from about 0.83 to about 1.0.

The present disclosure provides an article. In an embodiment, an article is provided and includes the composition composed of the random propylene/ethylene copolymer, and the substituted phenylene aromatic diester.

An advantage of the present disclosure is the provision of an improved random propylene/α-olefin copolymer composition.

An advantage of the present disclosure is the provision of a Ziegler-Natta catalyzed random propylene/α-olefin copolymer with increased random distribution of α-olefin units in the polymer chain.

An advantage of the present disclosure is the provision of a random propylene/α-olefin copolymer composition with improved melt strength.

An advantage of the present disclosure is the provision of a random propylene/α-olefin copolymer composition with improved optical properties.

An advantage of the present disclosure is the provision of a random propylene/α-olefin copolymer composition containing a substituted phenylene aromatic diester.

An advantage of the present disclosure is the provision of a random propylene/α-olefin copolymer that is phthalate-free.

DETAILED DESCRIPTION

The present disclosure provides a process. In an embodiment, a polymerization process is provided and includes contacting, under polymerization conditions, propylene and an α-olefin with a catalyst composition comprising a substituted phenylene aromatic diester. The process further includes forming a random propylene/ethylene copolymer having a Koening B-value from about 0.83 to about 1.0. In an embodiment, the Koenig B-value is from about 0.85 to about 1.0, or from about 0.89 to about 1.0.

It has been found that the monomer distribution may change based on the melt flow rate of the random copolymer produced via Ziegler-Natta catalyst composition. In an embodiment, the Koenig B-value is greater than or equal to $0.84 + 0.0266 \times \log 10$ (melt flow rate of the formant polymer).

The term "random propylene/α-olefin copolymer," as used herein, is a copolymer containing monomers of propylene and monomers of one or more α-olefin(s) polymerized together to form a polymer wherein the individual repeating units are present in a random or statistical distribution in the polymer chain. Ethylene is considered an α-olefin.

In an embodiment, the α-olefin is ethylene. The process further includes forming a "random propylene/ethylene copolymer" which is a polymer containing, in polymerized form, (i) a majority weight percent propylene monomer and (ii) ethylene monomer wherein the individual repeating units are present in a random or statistical distribution in the polymer chain.

As used herein, "a catalyst composition" is a composition that forms an olefin-based polymer when contacted with an olefin under polymerization conditions. The catalyst composition includes a procatalyst composition, a cocatalyst, optionally an external electron donor, and optionally an activity limiting agent. The procatalyst composition includes a combination of a magnesium moiety, a titanium moiety and an internal electron donor. The internal electron donor includes the substituted phenylene aromatic diester.

The procatalyst composition is produced by halogenating/titanating a procatalyst precursor in the presence of the internal electron donor. As used herein, an "internal electron donor" is a compound added or otherwise formed during formation of the procatalyst composition that donates at least one pair of electrons to one or more metals present in the resultant procatalyst composition. The internal electron donor is the substituted phenylene aromatic diester. Not wishing to be bound by any particular theory, it is believed that during halogenation and titanation the internal electron donor (1) regulates the formation of active sites, (2) regulates the position of titanium on the magnesium-based support and thereby enhances catalyst stereoselectivity, (3) facilitates conversion of the magnesium and titanium moieties into respective halides and (4) regulates the crystallite size of the magnesium halide support during conversion. Thus, provision of the internal electron donor yields a procatalyst composition with enhanced stereoselectivity.

The procatalyst precursor may be a magnesium moiety compound (MagMo), a mixed magnesium titanium compound (MagTi), or a benzoate-containing magnesium chloride compound (BenMag). In an embodiment, the procatalyst precursor is a magnesium moiety ("MagMo") precursor. The "MagMo precursor" contains magnesium as the sole metal component. The MagMo precursor includes a magnesium moiety. Nonlimiting examples of suitable magnesium moieties include anhydrous magnesium chloride and/or its alcohol adduct, magnesium alkoxide or aryloxide, mixed magnesium alkoxy halide, and/or carbonated magnesium dialkoxide or aryloxide. In one embodiment, the MagMo precursor is a magnesium di $(C_{1-4})$alkoxide. In a further embodiment, the MagMo precursor is diethoxymagnesium.

In an embodiment, the procatalyst precursor is a mixed magnesium/titanium compound ("MagTi"). The "MagTi precursor" has the formula $Mg_dTi(OR^e)_fX_g$ wherein $R^e$ is an aliphatic or aromatic hydrocarbon radical having 1 to 14 carbon atoms or COR' wherein R' is an aliphatic or aromatic hydrocarbon radical having 1 to 14 carbon atoms; each $OR^e$ group is the same or different; X is independently chlorine, bromine or iodine, preferably chlorine; d is 0.5 to 56, or 2 to 4; f is 2 to 116 or 5 to 15; and g is 0.5 to 116, or 1 to 3.

In an embodiment, the procatalyst precursor is a benzoate-containing magnesium chloride material. As used herein, a "benzoate-containing magnesium chloride" ("BenMag") is a magnesium chloride procatalyst (i.e., a halogenated procatalyst precursor) containing a benzoate internal electron donor. The BenMag material may also include a titanium moiety, such as a titanium halide. The benzoate internal donor is labile and can be replaced by other electron donors during procatalyst synthesis. Nonlimiting examples of suitable benzoate groups include ethyl benzoate, methyl benzoate, ethyl p-methoxybenzoate, methyl p-ethoxybenzoate, ethyl p-ethoxybenzoate, ethyl p-chlorobenzoate. In one embodiment, the benzoate group is ethyl benzoate. Nonlimiting examples of suitable BenMag procatalyst precursors include catalysts of the trade names SHAC™ 103 and SHAC™ 310 available from The Dow Chemical Company, Midland, Mich.

In an embodiment, the BenMag procatalyst precursor is a product of halogenation of any procatalyst precursor (i.e., a MagMo precursor or a MagTi precursor) in the presence of a benzoate compound with the structure (I)

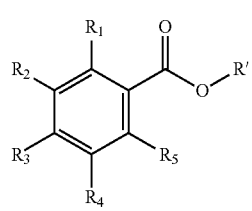

(I)

wherein $R_1$-$R_5$ are H, $C_1$-$C_{20}$ hydrocarbyl which may contain heteroatoms including F, Cl, Br, I, O, S, N, P, and Si, and R' is a $C_1$-$C_{20}$ hydrocarbyl group which may optionally contain heteroatom(s) including F, Cl, Br, I, O, S, N, P, and Si. Preferably, $R_1$-$R_5$ are selected from H and $C_1$-$C_{20}$ alkyl and R' is selected from $C_1$-$C_{20}$ alkyl and alkoxyalkyl.

Halogenation/titanation of the procatalyst precursor in the presence of the internal electron donor produces a procatalyst composition which includes a combination of a magnesium moiety, a titanium moiety, and the internal electron donor (a substituted phenylene aromatic diester). In an embodiment, the magnesium and titanium moieties are respective halides, such as magnesium chloride and titanium chloride. Bounded by no particular theory, it is believed that the magnesium halide is a support upon which the titanium halide is deposited and into which the internal electron donor is incorporated.

The resulting procatalyst composition has a titanium content of from about 1.0 percent by weight to about 6.0 percent by weight, based on the total weight of the procatalyst composition, or from about 1.0 percent by weight to about 5.5 percent by weight, or from about 2.0 percent by weight to about 5.0 percent by weight. The weight ratio of titanium to magnesium in the solid procatalyst composition is suitably between about 1:3 and about 1:160, or between about 1:4 and about 1:50, or between about 1:6 and 1:30. The internal electron donor is present in an amount from about 0.1 wt % to about 20.0 wt %, or from about 1.0 wt % to about 15 wt %. The substituted phenylene aromatic diester is present in the procatalyst composition in a molar ratio of internal electron donor to magnesium of from about 0.005:1 to about 1:1, or from about 0.01:1 to about 0.4:1. Weight percent is based on the total weight of the procatalyst composition.

Ethoxide content in the procatalyst composition indicates the completeness of conversion of precursor metal ethoxide into a metal halide. The substituted phenylene aromatic diester assists in converting ethoxide into halide during halogenation. In an embodiment, the procatalyst composition includes from about 0.01 wt % to about 1.0 wt %, or from about 0.05 wt % to about 0.5 wt % ethoxide. Weight percent is based on the total weight of the procatalyst composition.

In an embodiment, the internal electron donor is a mixed internal electron donor. As used herein, a "mixed internal electron donor" is (i) a substituted phenylene aromatic diester, (ii) an electron donor component that donates a pair of electrons to one or more metals present in the resultant procatalyst composition, and (iii) optionally other components. In an embodiment, the electron donor component is a benzoate, such as ethyl benzoate and/or methoxypropan-2-yl benzoate. The procatalyst composition with the mixed internal electron donor can be produced by way of the procatalyst production procedure as previously disclosed.

The internal electron donor includes the substituted phenylene aromatic diester and optionally an electron donor component. The substituted phenylene aromatic diester may be a substituted 1,2-phenylene aromatic diester, a substituted 1,3 phenylene aromatic diester, or a substituted 1,4 phenylene aromatic diester. In an embodiment, the internal electron donor is a 1,2-phenylene aromatic diester with the structure (II) below:

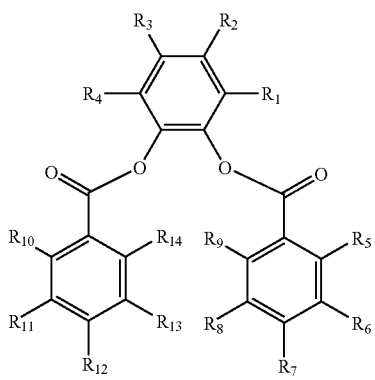

(II)

wherein $R_1$-$R_{14}$ are the same or different. Each of $R_1$-$R_{14}$ is selected from a hydrogen, substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof. At least one of $R_1$-$R_{14}$ is not hydrogen.

As used herein, the term "hydrocarbyl" and "hydrocarbon" refer to substituents containing only hydrogen and carbon atoms, including branched or unbranched, saturated or unsaturated, cyclic, polycyclic, fused, or acyclic species, and combinations thereof. Nonlimiting examples of hydrocarbyl groups include alkyl-, cycloalkyl-, alkenyl-, alkadienyl-, cycloalkenyl-, cycloalkadienyl-, aryl-, aralkyl, alkylaryl, and alkynyl-groups.

As used herein, the terms "substituted hydrocarbyl" and "substituted hydrocarbon" refer to a hydrocarbyl group that is substituted with one or more nonhydrocarbyl substituent groups. A nonlimiting example of a nonhydrocarbyl substituent group is a heteroatom. As used herein, a "heteroatom" refers to an atom other than carbon or hydrogen. The heteroatom can be a non-carbon atom from Groups IV, V, VI, and VII of the Periodic Table. Nonlimiting examples of heteroatoms include: halogens (F Cl, Br, I), N, O, P, B, S, and Si. A substituted hydrocarbyl group also includes a halohydrocarbyl group and a silicon-containing hydrocarbyl group. As used herein, the term "halohydrocarbyl" group refers to a hydrocarbyl group that is substituted with one or more halogen atoms. As used herein, the term "silicon-containing hydrocarbyl group" is a hydrocarbyl group that is substituted with one or more silicon atoms. The silicon atom(s) may or may not be in the carbon chain.

In an embodiment, at least one (or two, or three, or four) R group(s) of $R_1$-$R_4$ is selected from a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof.

In an embodiment, at least one (or some, or all) R group(s) of $R_5$-$R_{14}$ is selected from a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof. In another embodiment, at least one of $R_5$-$R_9$ and at least one of $R_{10}$-$R_{14}$ is selected from a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof.

In an embodiment, at least one of $R_1$-$R_4$ and at least one of $R_5$-$R_{14}$ is selected from a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof. In another embodiment, at least one of $R_1$-$R_4$ at least one $R_5$-$R_9$ of and at least one of $R_{10}$-$R_{14}$ is selected from a substituted hydrocarbyl group having 1 to 20 carbon atoms, an unsubstituted hydrocarbyl group having 1 to 20 carbon atoms, an alkoxy group having 1 to 20 carbon atoms, a heteroatom, and combinations thereof.

In an embodiment, any consecutive R groups in $R_1$-$R_4$, and/or any consecutive R groups in $R_5$-$R_9$, and/or any consecutive R groups in $R_{10}$-$R_{14}$ may be linked to form an inter-cyclic or an intra-cyclic structure. The inter-/intra-cyclic structure may or may not be aromatic. In an embodiment, the inter-/intra-cyclic structure is a $C_5$ or a $C_6$ membered ring.

In an embodiment, at least one of $R_1$-$R_4$ is selected from a substituted hydrocarbyl group having 1 to 20 carbon atoms, an unsubstituted hydrocarbyl group having 1 to 20 carbon atoms, and combinations thereof. Optionally, at least one of $R_5$-$R_{14}$ may be a halogen atom or an alkoxy group having 1 to 20 carbon atoms. Optionally, $R_1$-$R_4$, and/or $R_5$-$R_9$, and/or $R_{10}$-$R_{14}$ may be linked to form an inter-cyclic structure or an intra-cyclic structure. The inter-cyclic structure and/or the intra-cyclic structure may or may not be aromatic.

In an embodiment, any consecutive R groups in $R_1$-$R_4$, and/or in $R_5$-$R_9$, and/or in $R_{10}$-$R_{14}$, may be members of a $C_5$-$C_6$-membered ring.

In an embodiment, structure (II) includes $R_1$, $R_3$ and $R_4$ as hydrogen. $R_2$ is selected from a substituted hydrocarbyl group having 1 to 20 carbon atoms, an unsubstituted hydrocarbyl group having 1 to 20 carbon atoms, and combinations thereof. $R_5$-$R_{14}$ are the same or different and each of $R_5$-$R_{14}$ is selected from hydrogen, a substituted hydrocarbyl group having 1 to 20 carbon atoms, an unsubstituted hydrocarbyl group having 1 to 20 carbon atoms, an alkoxy group having 1 to 20 carbon atoms, a halogen, and combinations thereof.

In an embodiment, structure (II) includes $R_2$ that is methyl, and each of $R_5$-$R_{14}$ is hydrogen.

In an embodiment, structure (II) includes $R_2$ that is ethyl, and each of $R_5$-$R_{14}$ is hydrogen.

In an embodiment, structure (II) includes $R_2$ that is t-butyl, and each of $R_5$-$R_{14}$ is hydrogen.

In an embodiment, structure (II) includes $R_2$ that is ethoxycarbonyl, and each of $R_5$-$R_{14}$ is hydrogen.

In an embodiment, structure (II) includes $R_2$, $R_3$ and $R_4$ each as hydrogen and $R_1$ is selected from a substituted hydrocarbyl group having 1 to 20 carbon atoms, an unsubstituted hydrocarbyl group having 1 to 20 carbon atoms, and combinations thereof. $R_5$-$R_{14}$ are the same or different and each is selected from hydrogen, a substituted hydrocarbyl group having 1 to 20 carbon atoms, an unsubstituted hydrocarbyl group having 1 to 20 carbon atoms, an alkoxy group having 1 to 20 carbon atoms, a halogen, and combinations thereof.

In an embodiment, structure (II) includes $R_1$ that is methyl, and each of $R_5$-$R_{14}$ is hydrogen.

In an embodiment, structure (II) includes $R_2$ and $R_4$ that are hydrogen and $R_1$ and $R_3$ are the same or different. Each of $R_1$ and $R_3$ is selected from a substituted hydrocarbyl group having 1 to 20 carbon atoms, an unsubstituted hydrocarbyl group having 1 to 20 carbon atoms, and combinations thereof. $R_5$-$R_{14}$ are the same or different and each of $R_5$-$R_{14}$ is selected from a substituted hydrocarbyl group having 1 to 20 carbon atoms, an unsubstituted hydrocarbyl group having 1 to 20 carbon atoms, an alkoxy group having 1 to 20 carbon atoms, a halogen, and combinations thereof.

In an embodiment, structure (II) includes $R_1$ and $R_3$ that are the same or different. Each of $R_1$ and $R_3$ is selected from a $C_1$-$C_8$ alkyl group, a $C_3$-$C_6$ cycloalkyl group, or a substituted $C_3$-$C_6$ cycloalkyl group. $R_5$-$R_{14}$ are the same or different and each of $R_5$-$R_{14}$ is selected from hydrogen, a $C_1$-$C_8$ alkyl group, and a halogen. Nonlimiting examples of suitable $C_1$-$C_8$ alkyl groups include methyl, ethyl, n-propyl, isopropyl, n-butyl, i-butyl, t-butyl, n-pentyl, i-pentyl, neopentyl, t-pentyl, n-hexyl, and 2,4,4-trimethylpentan-2-yl group. Nonlimiting examples of suitable $C_3$-$C_6$ cycloalkyl groups include cyclopentyl and cyclohexyl groups. In a further embodiment, at least one of $R_5$-$R_{14}$ is a $C_1$-$C_6$ alkyl group or a halogen.

In an embodiment, structure (II) includes $R_1$ that is a methyl group and $R_3$ that is a t-butyl group. Each of $R_2$, $R_4$ and $R_5$-$R_{14}$ is hydrogen.

In an embodiment, structure (II) includes $R_1$ and $R_3$ that is an isopropyl group. Each of $R_2$, $R_4$ and $R_5$-$R_{14}$ is hydrogen.

In an embodiment, structure (II) includes each of $R_1$, $R_5$, and $R_{10}$ as a methyl group and $R_3$ is a t-butyl group. Each of $R_2$, $R_4$, $R_6$-$R_9$ and $R_{11}$-$R_{14}$ is hydrogen.

In an embodiment, structure (II) includes each of $R_1$, $R_7$, and $R_{12}$ as a methyl group and $R_3$ is a t-butyl group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ as a methyl group and $R_3$ is a t-butyl group. Each of $R_7$ and $R_{12}$ is an ethyl group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes each of $R_1$, $R_5$, $R_7$, $R_9$, $R_{10}$, $R_{12}$, and $R_{14}$ as a methyl group and $R_3$ is a t-butyl group. Each of $R_2$, $R_4$, $R_6$, $R_8$, $R_{11}$, and $R_{13}$ is hydrogen.

In an embodiment, structure (II) includes $R_1$ as a methyl group and $R_3$ is a t-butyl group. Each of $R_5$, $R_7$, $R_9$, $R_{10}$, $R_{12}$, and $R_{14}$ is an i-propyl group. Each of $R_2$, $R_4$, $R_6$, $R_8$, $R_{11}$, and $R_{13}$ is hydrogen.

In an embodiment, the substituted phenylene aromatic diester has a structure (III) which includes $R_1$ that is a methyl group and $R_3$ is a t-butyl group. Each of $R_2$ and $R_4$ is hydrogen. $R_8$ and $R_9$ are members of a $C_6$ membered ring to form a 1-naphthoyl moiety. $R_{13}$ and $R_{14}$ are members of a $C_6$ membered ring to form another 1-naphthoyl moiety. Structure (III) is provided below.

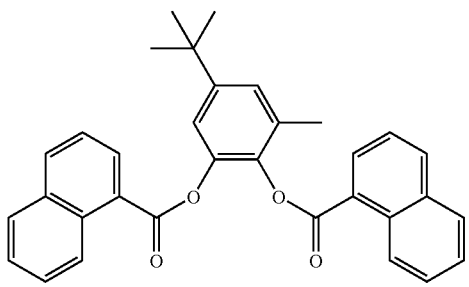

(III)

In an embodiment, the substituted phenylene aromatic diester has a structure (IV) which includes $R_1$ that is a methyl group and $R_3$ is a t-butyl group. Each of $R_2$ and $R_4$ is hydrogen. $R_6$ and $R_7$ are members of a $C_6$ membered ring to form a 2-naphthoyl moiety. $R_{12}$ and $R_{13}$ are members of a $C_6$ membered ring to form a 2-naphthoyl moiety. Structure (IV) is provided below.

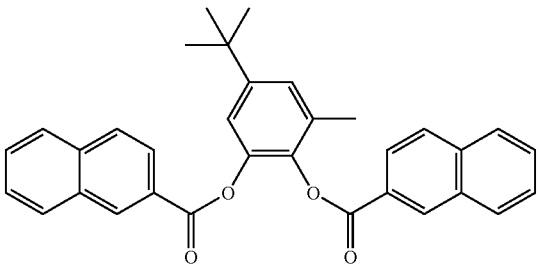

(IV)

In an embodiment, structure (II) includes $R_1$ that is a methyl group and $R_3$ is a t-butyl group. Each of $R_7$ and $R_{12}$ is an ethoxy group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is a fluorine atom. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is a chlorine atom. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is a bromine atom. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is an iodine atom. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_6$, $R_7$, $R_{11}$, and $R_{12}$ is a chlorine atom. Each of $R_2$, $R_4$, $R_5$, $R_8$, $R_9$, $R_{10}$, $R_{13}$, and $R_{14}$ is hydrogen.

In an embodiment, structure (II) includes $R_1$ that is a methyl group and $R_3$ is a t-butyl group. Each of $R_6$, $R_8$, $R_{11}$, and $R_{13}$ is a chlorine atom. Each of $R_2$, $R_4$, $R_5$, $R_7$, $R_9$, $R_{10}$, $R_{12}$, and $R_{14}$ is hydrogen.

In an embodiment, structure (II) include $R_1$ that is a methyl group and $R_3$ is a t-butyl group. Each of $R_2$, $R_4$ and $R_5$-$R_{14}$ is a fluorine atom.

In an embodiment, structure (II) includes $R_1$ that is a methyl group and $R_3$ is a t-butyl group. Each of $R_7$ and $R_{12}$ is a trifluoromethyl group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is an ethoxycarbonyl group. Each of $R_2$, $R_4$, $R_5$, $R_6$, $R_8$, $R_9$, $R_{10}$, $R_{11}$, $R_{13}$, and $R_{14}$ is hydrogen.

In an embodiment, $R_1$ is methyl group and $R_3$ is a t-butyl group. Each of $R_7$ and $R_{12}$ is an ethoxy group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a t-butyl group. Each of $R_7$ and $R_{12}$ is an diethylamino group. Each of $R_2$, $R_4$, $R_5$, $R_6$, $R_8$, $R_9$, $R_{10}$, $R_{11}$, $R_{13}$, and $R_{14}$ is hydrogen.

In an embodiment, structure (II) includes $R_1$ that is a methyl group and $R_3$ is a 2,4,4-trimethylpentan-2-yl group. Each of $R_2$, $R_4$ and $R_5$-$R_{14}$ is hydrogen.

In an embodiment, structure (II) includes $R_1$ and $R_3$, each of which is a sec-butyl group. Each of $R_2$, $R_4$ and $R_5$-$R_{14}$ is hydrogen.

In an embodiment, the substituted phenylene aromatic diester has a structure (V) whereby $R_1$ and $R_2$ are members of a $C_6$ membered ring to form a 1,2-naphthalene moiety. Each of $R_5$-$R_{14}$ is hydrogen. Structure (V) is provided below.

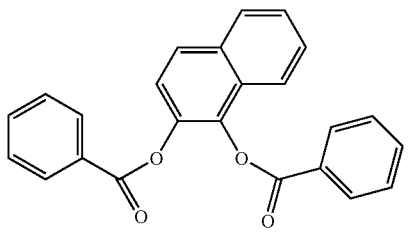

(V)

In an embodiment, the substituted phenylene aromatic diester has a structure (VI) whereby $R_2$ and $R_3$ are members of a $C_6$ membered ring to form a 2,3-naphthalene moiety. Each of $R_5$-$R_{14}$ is hydrogen. Structure (VI) is provided below.

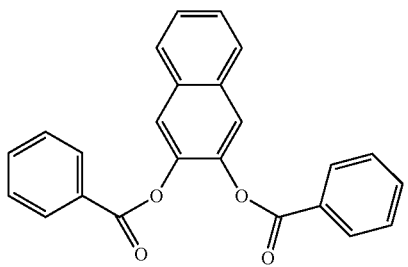

(VI)

In an embodiment, structure (II) includes $R_1$ and $R_4$ that are each a methyl group. Each of $R_2$, $R_3$, $R_5$-$R_9$ and $R_{10}$-$R_{14}$ is hydrogen.

In an embodiment, structure (II) includes $R_1$ that is a methyl group. $R_4$ is an i-propyl group. Each of $R_2$, $R_3$, $R_5$-$R_9$ and $R_{10}$-$R_{14}$ is hydrogen.

In an embodiment, structure (II) includes $R_1$, $R_3$, and $R_4$, each of which is an i-propyl group. Each of $R_2$, $R_5$-$R_9$ and $R_{10}$-$R_{14}$ is hydrogen.

The catalyst composition includes a cocatalyst. As used herein, a "cocatalyst" is a substance capable of converting the procatalyst to an active polymerization catalyst. The cocatalyst may include hydrides, alkyls, or aryls of aluminum, lithium, zinc, tin, cadmium, beryllium, magnesium, and combinations thereof. In an embodiment, the cocatalyst is a hydrocarbyl aluminum compound represented by the formula $R_n AlX_{3-n}$, wherein n=1 2, or 3, R is an alkyl, and X is a halide or alkoxide. Nonlimiting examples of suitable cocatalyst include from trimethylaluminum, triethylaluminum, tri-isobutylaluminum, and tri-n-hexylaluminum.

In an embodiment, the cocatalyst is triethylaluminum. The molar ratio of aluminum to titanium is from about 5:1 to about 500:1, or from about 10:1 to about 200:1, or from about 15:1 to about 150:1, or from about 20:1 to about 100:1, or from about 30:1 to about 60:1. In another embodiment, the molar ratio of aluminum to titanium is about 35:1.

In an embodiment, the present catalyst composition includes an external electron donor. As used herein, an "external electron donor" (or "EED") is a compound added independent of procatalyst formation and includes at least one functional group that is capable of donating a pair of electrons to a metal atom. A "mixed external electron donor" (or "MEED") is a mixture of two or more external electron donors. Bounded by no particular theory, it is believed that provision of one or more external electron donors in the catalyst composition affects the following properties of the formant polymer: level of tacticity (i.e., xylene soluble material), molecular weight (i.e., melt flow), molecular weight distribution (MWD), melting point, and/or oligomer level.

In an embodiment, the external electron donor may be selected from one or more of the following: a silicon compound, a bidentate compound, an amine, an ether, a carboxylate, a ketone, an amide, a carbamate, a phosphine, a phosphate, a phosphite, a sulfonate, a sulfone, a sulfoxide, and any combination of the foregoing.

In an embodiment, the EED is a silicon compound having the general formula (VII):

$$SiR_m(OR')_{4-m} \qquad (VII)$$

wherein R independently each occurrence is hydrogen or a hydrocarbyl or an amino group, optionally substituted with one or more substituents containing one or more Group 14, 15, 16, or 17 heteroatoms. R contains up to 20 atoms not counting hydrogen and halogen. R' is a $C_{1-20}$ alkyl group, and m is 0, 1, or 2. In an embodiment, R is $C_{6-12}$ aryl, alkylaryl or aralkyl, $C_{3-12}$ cycloallyl, $C_{1-20}$ linear alkyl or alkenyl, $C_{3-12}$ branched alkyl, or $C_{3-12}$ cyclic amino group, R' is $C_{1-4}$ alkyl, and m is 1 or 2.

Nonlimiting examples of suitable silicon compounds for the EED include dialkoxysilanes, trialkoxysilanes, and tetraalkoxysilanes such as dicyclopentyldimethoxysilane, diisopropyldimethoxysilane, bis(perhydroisoquinolino)dimethoxysilane, methylcyclohexyldimethoxysilane, tetraethoxysilane, n-propyltrimethoxysilane, n-propyltriethoxysilane, diethylaminotriethoxysilane, bis(trimethylsilylmethyl)dimethoxysilane, and any combination thereof.

In an embodiment, the catalyst composition includes an activity limiting agent (ALA). As used herein, an "activity limiting agent" ("ALA") is a material that reduces catalyst activity at elevated temperature (i.e., temperature greater than about 85° C.). An ALA inhibits or otherwise prevents polymerization reactor upset and ensures continuity of the polymerization process. Typically, the activity of Ziegler-Natta catalysts increases as the reactor temperature rises. Ziegler-Natta catalysts also typically maintain high activity near the softening point temperature of the polymer produced. The heat generated by the exothermic polymerization reaction may cause polymer particles to form agglomerates and may ultimately lead to disruption of continuity for the polymer production process. The ALA reduces catalyst activity at elevated temperature, thereby preventing reactor upset, reducing (or preventing) particle agglomeration, and ensuring continuity of the polymerization process.

The ALA may or may not be a component of the EED and/or the MEED. The activity limiting agent may be a carboxylic acid ester, a diether, a poly(alkene glycol), a succinate, a diol ester, and combinations thereof. The carboxylic acid ester can be an aliphatic or aromatic, mono- or poly-carboxylic acid ester. Nonlimiting examples of suitable carboxylic acid esters include benzoates, $C_{1-40}$ alkyl esters of aliphatic $C_{2-40}$ mono-/di-carboxylic acids, $C_{2-40}$ mono-/poly-carboxylate derivatives of $C_{2-100}$ (poly)glycols, $C_{2-100}$ (poly)glycol ethers, and any combination thereof. Further nonlimiting examples of carboxylic acid esters include laurates, myristates, palmitates, stearates, oleates, sebacates, and (poly)(alkylene)glycols, and mixtures thereof. In a further embodiment, the ALA is isopropyl myristate or di-n-butyl sebacate.

The catalyst composition may include any of the foregoing external electron donors in combination with any of the foregoing activity limiting agents. The external electron donor and/or activity limiting agent can be added into the reactor separately. Alternatively, the external electron donor and the activity limiting agent can be mixed together in advance and then added to the catalyst composition and/or into the reactor as a mixture.

The process includes contacting, under polymerization conditions, propylene and ethylene with the catalyst composition containing the substituted phenylene aromatic diester. As used herein, "polymerization conditions" are temperature and pressure parameters within a polymerization reactor suitable for promoting polymerization between the catalyst composition and an olefin to form the desired polymer. The polymerization process may be a gas phase, a slurry, or a bulk polymerization process, operating in one, or more than one, reactor.

It is understood that provision of hydrogen in the polymerization reactor is a component of the polymerization conditions. During polymerization, hydrogen is a chain transfer agent and affects the molecular weight (and correspondingly the melt flow rate) of the resultant polymer. The polymerization process may include a pre-polymerization step and/or a pre-activation step.

One or more olefin comonomers can be introduced into a polymerization reactor along with the propylene to react with the catalyst and to form a polymer, or a fluidized bed of polymer particles. Nonlimiting examples of suitable olefin monomers include ethylene (for purposes of this disclosure, ethylene is considered an α-olefin), $C_{4-20}$ α-olefins, such as 1-butene, 1-pentene, 1-hexene, 4-methyl-1-pentene, 1-heptene, 1-octene, 1-decene, 1-dodecene and the like. In an embodiment, the olefin comonomer is ethylene.

The process includes forming a random propylene/ethylene copolymer having a Koening B-value from about 0.83 to about 1.0 or from about 0.85 to about 1.0, or from about 0.89 to about 1.0. The random propylene/ethylene copolymer includes the substituted phenylene aromatic diester. Applicants surprisingly discovered that provision of the substituted phenylene aromatic diester in the catalyst composition unexpectedly forms a propylene/ethylene copolymer with a Koening B-value from about 0.83 to about 1.0. The term "B-Value" is a measurement of the comonomer distribution across a polymer chain. The "Koening B-Value" calculates the distribution of the ethylene units of a copolymer of propylene and ethylene, or a copolymer of propylene, ethylene and at least one unsaturated comonomer, across the polymer chain. Koening B-values range from 0 to 2 with 1 designating a perfectly random distribution of comonomer units. The higher the Koening B-value, the more alternating the comonomer distribution in the copolymer. The lower the Koenig B-value, the more blocky or clustered the comonomer distribution in the copolymer.

The Koenig B-Value is determined according to the method of J. L. Koenig (Spectroscopy of Polymers, $2^{nd}$ Edition, Elsevier, 1999). B is defined for a propylene/ethylene copolymer as:

$$B = \frac{f(EP + PE)}{2 \cdot F_E \cdot F_P}$$

where f(EP+PE)=the sum of the EP and PE diad fractions; FE and FP=the mole fraction of ethylene and propylene in the copolymer, respectively. The diad fraction can be derived from triad data according to: f(EP+PE)=[EPE]+[EPP+PPE]/2+[PEP]+[EEP+PEE]/2. The Koenig B-values can be calculated for other copolymers in an analogous manner by assignment of the respective copolymer diads. For example, calculation of the B-value for propylene/1-octene copolymer uses the following equation $$B = \frac{f(OP + PO)}{2 \cdot F_O \cdot F_P}$$

The present propylene/ethylene copolymer containing the substituted phenylene aromatic diester has a greater Koening B-value (i.e., greater randomness in comonomer distribution) than the same, or substantially the same, Ziegler-Natta catalyzed propylene/ethylene composition except that the procatalyst composition has a different internal electron donor. For example, the Koening B-value for the present propylene/ethylene copolymer (made with substituted phenylene aromatic diester internal electron donor) is greater than the Koening B-value for a similar or comparable Ziegler-Natta catalyzed propylene/ethylene copolymer made with a phthalate-based internal electron donor.

The present process produces a composition. In an embodiment, a composition is provided and includes a random propylene/ethylene copolymer. The propylene/ethylene random copolymer includes a substituted phenylene aromatic diester.

In an embodiment, the random propylene/ethylene copolymer has a Koening B-value from about 0.83 to about 1.0 as previously disclosed.

In an embodiment, the substituted phenylene aromatic diester of the composition is 3-methyl-5-tert butyl-1,2-phenylene dibenzoate.

In an embodiment, the random propylene/ethylene copolymer contains from about 0.1 wt % to about 10 wt %, or from about 0.3 wt % to about 7 wt %, or from about 1 wt % to about 5 wt % units derived from ethylene.

In an embodiment, the process includes maintaining a $H_2/C_3$ molar ratio from 0.002 to 0.02 during polymerization. This forms a "low melt flow random propylene/ethylene copolymer" having a melt flow rate (MFR) from 0.1 g/10 min to 5 g/10 min, or from 0.1 g/10 min to 1.0 g/10 min, or from 0.1 g/10 min to 0.5 g/10 min, or from 0.1 g/10 min to 0.2 g/10 min as measured in accordance with ASTM D 1238 using a 2.16 kg weight, and measured at 230° C. The low melt flow random propylene/ethylene copolymer has a PDI greater than 4.0, or greater than 5.0; a Koening B-value from about 0.88 to about 0.94, a xylene solubles content less than 9%, and a EEE triads less than 0.0075, or less than 0.005, or less than 0.004, or from about 0.003 to less than 0.0075. The "EEE triads" are the sequences of three molecules derived from ethylene that are adjacent to each other in the polymer chain.

In an embodiment, the polymerization process includes maintaining a $H_2/C_3$ molar ratio from 0.010 to 0.25 and forming a "high melt flow random propylene/ethylene copolymer" having a MFR from greater than 5 g/10 min to about 800 g/10 min, or from 60 g/10 min to 700 g/10 min, or from 100 g/10 min to 600 g/10 min as measured in accordance with ASTM D 1238 2.16, 230° C. The high melt flow propylene/ethylene copolymer has a PDI less than 5.0, or from about 4.0 to less than 5.0, a Koenig B-value from about 0.88 to about 0.94, a xylene solubles content less than 9%, or less than 6%, and a EEE triads 0.005 or less than 0.004, or from about 0.002 to about 0.005.

In an embodiment, the composition is molded into a plaque. The plaque has one or more of the following properties: a haze value less than 15%, or less than 10%, or less than 9%, or from about 7% to less than about 15%; and/or a clarity greater than 97%, or greater than 98%.

In an embodiment, the random propylene/ethylene copolymer may or may not be visbroken. "Visbreaking" (or "visbroken" or "cracking or cracked") is a process which subjects the propylene polymer to chain scission. The visbreaking process lowers the molecular weight and raises the melt flow rate. The visbreaking process also leads to a narrowing of the molecular weight distribution. The present random propylene/ethylene copolymer may or may not be visbroken or cracked.

In an embodiment, the composition may include one or more of the following additives: stabilizers, lubricants, mold release agents, fillers, nucleating agents, antistatics, plasticizers, dyes, pigments, antifungals, anti-microbial agents, film cavitating agents, flame retardants, and any combination of the foregoing.

In an embodiment, the present random propylene/ethylene copolymer is phthalate-free.

The present polymerization process and/or the present composition may comprise two or more embodiments disclosed herein.

The composition may be formed into an article. In an embodiment, an article is provided and includes a composition of random propylene/ethylene copolymer and a substituted phenylene aromatic diester. The composition is any of the foregoing random propylene/ethylene copolymers.

In an embodiment, the article is a molded article. The molded article may be an extruded article, an injection molded article, a blow molded article, a rotation molded article, and a thermoformed article. "Molding" is a process by which a polymer is melted and led into a mold, which is the inverse of the desired shape, to form parts of the desired shape and size. Molding can be pressure-less or pressure-assisted.

"Extrusion" (including sheet extrusion and profile extrusion) is a process by which a polymer is propelled continuously along a screw through regions of high temperature and pressure where it is melted and compacted, and finally forced through a die. The extruder can be a single screw extruder, a multiple screw extruder, a disk extruder or a ram extruder. The die can be a film die, blown film die, sheet die, pipe die, tubing die or profile extrusion die. Nonlimiting examples of extruded articles include pipe, film, and/or fibers.

"Injection molding" is a process by which a polymer is melted and injected at high pressure into a mold, which is the inverse of the desired shape, to form parts of the desired shape and size. The mold can be made from metal, such as steel and aluminum. "Rotational molding" is a process used for producing hollow plastic products. Rotational molding differs from other processing methods in that the heating, melting, shaping, and cooling stages all occur after the polymer is placed in the mold, therefore no external pressure is applied during forming.

"Blow molding" is a process for making hollow plastics containers. Blow molding includes placing a softened polymer in the center of a mold, inflating the polymer against the mold walls with a blow pin, and solidifying the product by cooling. There are three general types of blow molding: extrusion blow molding, injection blow molding, and stretch blow molding. Injection blow molding can be used to process polymers that cannot be extruded. Stretch blow molding can be used for difficult to blow crystalline and crystallizable polymers such as polypropylene.

Applicants have surprisingly discovered that provision of the substituted phenylene aromatic diester in the procatalyst composition advantageously increases molecular weight the distribution of the formant polymer compared to polymers with the same, or substantially the same, monomer/comonomer content, and the same, or substantially the same melt flow rate. In addition, the substituted phenylene aromatic diester unexpectedly increases the randomness of comonomer distribution in the present random propylene/ethylene copolymer. This leads to improved stiffness and/or improved optical properties in the present random propylene/ethylene copolymer.

Many processing operations require a polymer to have a suitable melt strength. In particular, many processing operations require a polymer to either retain its shape or not to break while the polymer is in the liquid phase. For example, during the blow molding process a parison is extruded, and this parison must have enough strength not to break or fall off the die before it is blow molded. Or, as in the production of pipe, for example, it is desirable for the pipe to keep its round shape as the pipe cools and becomes solid.

In an embodiment, the present low melt flow propylene/ethylene copolymer has a melt strength greater than 40 cN, or greater than 44 cN, or greater than 40 cN to about 50 cN. Bounded by no particular theory, it is believed that the provision of the substituted phenylene aromatic diester during polymerization increases the molecular weight distribution (increases the PDI) of the formant polymer which correspondingly increases the melt strength at a given melt flow rate.

In an embodiment, the molded article made from the low melt flow propylene/ethylene copolymer is a pipe, such as an extruded pipe. During the production of pipe and other extruded articles, melt strength is needed for the pipe to keep its round shape. Additionally, it is desired for the production process to proceed rapidly. The increased molecular weight distribution in the present random propylene/ethylene copolymer improves the shear-thinning of extruded articles thereby allowing the extruded article to come out of the extruder faster. In addition, the present random propylene/ethylene copolymer with improved shear-thinning requires less power for the extrusion process. The present random propylene/ethylene copolymer with increased random distribution of the comonomer may provide improved hydrostatic burst resistance to the pipe. Furthermore, with increased randomness, it is possible to use less ethylene in the production of the pipe, leading to a stiffer product.

The increased randomness of comonomer distribution in the present high melt flow propylene/ethylene copolymer unexpectedly improves the optical properties for molded articles made therefrom. In an embodiment, an injection molded article composed of the high melt flow propylene/ethylene copolymer has a haze value less than 15%, or less than 10%, or less than 9%, or from about 7% to less than 15% as measured in accordance with ASTM D 1003; and/or a clarity greater 97%, or than 98%, or greater than 99% (as measured in accordance with ASTM D 1746); and/or a gloss value greater than 90 as measured in accordance with ASTM D 523 (45°).

In an embodiment, the procatalyst composition, the polymer composition produced therefrom, and/or articles composed of the polymeric composition produced from the procatalyst composition is/are phthalate-free, or is/are otherwise void or devoid of phthalate and/or phthalate derivatives.

The present article may comprise two or more embodiments disclosed herein.

Definitions

All references to the Periodic Table of the Elements herein shall refer to the Periodic Table of the Elements, published and copyrighted by CRC Press, Inc., 2003. Also, any references to a Group or Groups shall be to the Groups or Groups reflected in this Periodic Table of the Elements using the IUPAC system for numbering groups. Unless stated to the contrary, implicit from the context, or customary in the art, all parts and percents are based on weight. For purposes of United States patent practice, the contents of any patent, patent application, or publication referenced herein are hereby incorporated by reference in their entirety (or the equivalent US version thereof is so incorporated by reference), especially with respect to the disclosure of synthetic techniques, definitions (to the extent not inconsistent with any definitions provided herein) and general knowledge in the art.

The term "comprising," and derivatives thereof, is not intended to exclude the presence of any additional component, step or procedure, whether or not the same is disclosed herein. In order to avoid any doubt, all compositions claimed herein through use of the term "comprising" may include any additional additive, adjuvant, or compound whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination.

Any numerical range recited herein, includes all values from the lower value to the upper value, in increments of one unit, provided that there is a separation of at least 2 units between any lower value and any higher value. As an example, if it is stated that the amount of a component, or a value of a compositional or a physical property, such as, for example, amount of a blend component, softening temperature, melt index, etc., is between 1 and 100, it is intended that all individual values, such as, 1, 2, 3, etc., and all subranges, such as, 1 to 20, 55 to 70, 197 to 100, etc., are expressly enumerated in this specification. For values which are less than one, one unit is considered to be 0.0001, 0.001, 0.01 or 0.1, as appropriate. These are only examples of what is specifically intended, and all possible combinations of numerical values between the lowest value and the highest value enumerated, are to be considered to be expressly stated in this application. In other words, any numerical range recited herein includes any value or subrange within the stated range. Numerical ranges have been recited, as discussed herein, reference melt index, melt flow rate, and other properties.

The terms "blend" or "polymer blend," as used herein, is a blend of two or more polymers. Such a blend may or may not be miscible (not phase separated at molecular level). Such a blend may or may not be phase separated. Such a blend may or may not contain one or more domain configurations, as determined from transmission electron spectroscopy, light scattering, x-ray scattering, and other methods known in the art.

The term "composition," as used herein, includes a mixture of materials which comprise the composition, as well as reaction products and decomposition products formed from the materials of the composition.

The term "polymer" is a macromolecular compound prepared by polymerizing monomers of the same or different type. "Polymer" includes homopolymers, copolymers, terpolymers, interpolymers, and so on. The term "interpolymer" means a polymer prepared by the polymerization of at least two types of monomers or comonomers. It includes, but is not limited to, copolymers (which usually refers to polymers prepared from two different types of monomers or comonomers, terpolymers (which usually refers to polymers prepared from three different types of monomers or comonomers), tetrapolymers (which usually refers to polymers prepared from four different types of monomers or comonomers), and the like.

The term "olefin-based polymer" is a polymer containing, in polymerized form, a majority weight percent of an olefin, for example ethylene or propylene, based on the total weight of the polymer. Nonlimiting examples of olefin-based polymers include ethylene-based polymers and propylene-based polymers.

The term, "propylene-based polymer," as used herein, is a polymer that comprises a majority weight percent polymerized propylene monomer (based on the total amount of polymerizable monomers), and optionally may comprise at least one polymerized comonomer.

The term "alkyl," as used herein, refers to a branched or unbranched, saturated or unsaturated acyclic hydrocarbon radical. Nonlimiting examples of suitable alkyl radicals include, for example, methyl, ethyl, n-propyl, i-propyl, 2-propenyl (or allyl), vinyl, n-butyl, t-butyl, i-butyl (or 2-methylpropyl), etc. The alkyls have 1 and 20 carbon atoms.

The term "substituted alkyl," as used herein, refers to an alkyl as just described in which one or more hydrogen atom bound to any carbon of the alkyl is replaced by another group such as a halogen, aryl, substituted aryl, cycloalkyl, substituted cycloalkyl, heterocycloalkyl, substituted heterocycloalkyl, halogen, haloalkyl, hydroxy, amino, phosphido, alkoxy, amino, thio, nitro, and combinations thereof. Suitable substituted alkyls include, for example, benzyl, trifluoromethyl and the like.

The term "aryl," as used herein, refers to an aromatic substituent which may be a single aromatic ring or multiple aromatic rings which are fused together, linked covalently, or linked to a common group such as a methylene or ethylene moiety. The aromatic ring(s) may include phenyl, naphthyl, anthracenyl, and biphenyl, among others. The aryls have 1 and 20 carbon atoms.

Test Methods $^{13}C$ NMR characterization (ethylene content, Koenig B-value, triad distribution, triad tacticity, number average sequence length for ethylene and propylene (i.e., le and lp respectively) is performed as follows:

Sample Preparation

The samples are prepared by adding approximately 2.7 g of a 50/50 mixture of tetrachloroethane-$d_2$/orthodichlorobenzene containing 0.025 M Cr(AcAc)$_3$ to 0.20 g sample in a Norell 1001-7 10 mm NMR tube. The samples are dissolved and homogenized by heating the tube and its contents to 150° C. using a heating block and heat gun. Each sample is visually inspected to ensure homogeneity.

Data Acquisition Parameters

The data are collected using a Bruker 400 MHz spectrometer equipped with a Bruker Dual DUL high-temperature CryoProbe. The data are acquired using 1280 transients per data file, a 6 sec pulse repetition delay, 90 degree flip angles, and inverse gated decoupling with a sample temperature of 120° C. All measurements are made on non-spinning samples in locked mode. Samples are allowed to thermally equilibrate for 7 minutes prior to data acquisition Differential Scanning Calorimetry (DSC) is used to determine the melting point (Tm), the crystallization temperature (Tc) and the heat of fusion (ΔHf). In this method, the sample is heated quickly and then held at 220° C. for a period of 5 minutes to ensure that all crystallites have melted. The sample is then cooled at 10° C./min from 220° C. to 0° C., and held at 0° C. for 5 minutes. Subsequently, the sample is reheated at 10° C./min from 0° C. to 220° C.

Flexural modulus (1% SFM) is determined in accordance with ASTM D790-00 Method I, using an ASTM D 638 Type 1 injection molded specimen tested at 1.3 mm/min.

Gel Permeation Chromatography (GPC) Analytical Method for Polypropylene. The polymers are analyzed on a PL-220 series high temperature gel permeation chromatography (GPC) unit equipped with a refractometer detector and four PLgel Mixed-A (20 µm) columns (Polymer Laboratory Inc.). The oven temperature is set at 150° C. and the temperatures of autosampler's hot and the warm zones are at 135° C. and 130° C. respectively. The solvent is nitrogen purged 1,2,4-trichlorobenzene (TCB) containing ~200 ppm 2,6-di-t-butyl-4-methylphenol (BHT). The flow rate is 1.0 mL/min and the injection volume was 200 µl. A 2 mg/mL sample concentration is prepared by dissolving the sample in $N_2$ purged and preheated TCB (containing 200 ppm BHT) for 2.5 hrs at 160° C. with gentle agitation.

Gloss (45°) is measured in accordance with ASTM D2457, using 1 mm injection molded plaques.

The GPC column set is calibrated by running twenty narrow molecular weight distribution polystyrene standards. The molecular weight (MW) of the standards ranges from 580 to 8,400,000 g/mol, and the standards were contained in 6 "cocktail" mixtures. Each standard mixture has at least a decade of separation between individual molecular weights. The polystyrene standards are prepared at 0.005 g in 20 mL of solvent for molecular weights equal to or greater than 1,000,000 g/mol and 0.001 g in 20 mL of solvent for molecular weights less than 1,000,000 g/mol. The polystyrene standards are dissolved at 150° C. for 30 min under stirring. The narrow standards mixtures are run first and in order of decreasing highest molecular weight component to minimize degradation effect. A logarithmic molecular weight calibration is generated using a forth-order polynomial fit as a function of elution volume. The equivalent polypropylene molecular weights are calculated by using following equation with reported Mark-Houwink coefficients for polypropylene (Th. G. Scholte, N. L. J. Meijerink, H. M. Schoffeleers, and A. M. G. Brands, J. Appl. Polym. Sci., 29, 3763-3782 (1984)) and polystyrene (E. P. Otocka, R. J. Roe, N. Y. Hellman, P. M. Muglia, Macromolecules, 4, 507 (1971)):

$$M_{PP} = \left(\frac{K_{PS}M_{PS}^{a_{PS}+1}}{K_{PP}}\right)^{\frac{1}{a_{PP}+1}}$$

where $M_{PP}$ is PP equivalent MW, $M_{PS}$ is PS equivalent MW, log K and a values of Mark-Houwink coefficients for PP and PS are listed below.

| Polymer | a | log K |
|---|---|---|
| Polypropylene | 0.725 | −3.721 |
| Polystyrene | 0.702 | −3.900 |

Haze and Clarity are measured in accordance with ASTM D1003 on 1 mm injection molded plaques. Samples are compounded by extrusion at 235° C. Plaques for optical properties are injection molded at 200° C.

Izod impact strength is measured in accordance with ASTM D256.

Melt flow rate (MFR) is measured in accordance with ASTM D 1238-01 test method at 230° with a 2.16 kg weight for propylene-based polymers.

Molecular weights (Mn, Mw and Mz) and MWD's (Mw/Mn and Mz/Mw) are measured by GPC. Polystyrene standards is used for calibration.

Oligomer content is measured via a Gas Chromatography method which extracts the low molecular weight species with chloroform, and measures the oligomers that have between 12 and 21 carbon units. Hexadecane is used as a calibration standard.

Polydispersity Index (PDI) is measured using a Rheometrics 800 cone and plate rheometer from TA Instruments, operated at 180° C., using the method of Ziechner and Patel, (1981) "A Comprehensive Study of Polypropylene Melt Rheology" Proc. Of the $2^{nd}$ World Congress of Chemical Eng., Montreal, Canada. In this method the cross-over modulus is determined, and the PDI defined as 100,000/cross-over modulus (in Pascals).

Xylene Solubles (XS) is measured according to the following procedure. 0.4 g of polymer is dissolved in 20 ml of xylenes with stirring at 130° C. for 30 minutes. The solution is then cooled to 25° C. and after 30 minutes the insoluble polymer fraction is filtered off. The resulting filtrate is analyzed by Flow Injection Polymer Analysis using a Viscotek ViscoGEL H-100-3078 column with THF mobile phase flowing at 1.0 ml/min. The column is coupled to a Viscotek Model 302 Triple Detector Array, with light scattering, viscometer and refractometer detectors operating at 45° C. Instrument calibration was maintained with Viscotek PolyCAL™ polystyrene standards.

Melt strength is measured at 190° C. using a Göettfert Rheotens 71.97 (Göettfert Inc.; Rock Hill, S.C.), melt fed with a Göettfert Rheotester 2000 capillary rheometer equipped with a flat entrance angle (180 degrees) of length of 30 mm and diameter of 2 mm. The pellets are fed into the barrel (L=300 mm, Diameter=12 mm), compressed and allowed to melt for 10 minutes before being extruded at a constant piston speed of 0.265 mm/s, which corresponds to a wall shear rate of 38.2 $s^{-1}$ at the given die diameter. The extrudate passed through the wheels of the Rheotens located at 100 mm below the die exit and was pulled by the wheels downward at an acceleration rate of 2.4 mm/$s^2$. The force (in cN) exerted on the wheels was recorded as a function of the velocity of the wheels (in mm/s). Melt strength is reported as the peak or the plateau force (cN) before the strand breaks.

By way of example and not by limitation, examples of the present disclosure will now be provided.

EXAMPLES

1. Substituted Phenylene Aromatic Diester.

Substituted phenylene aromatic diester may be synthesized in accordance with provisional U.S. patent application Ser. No. 61/141,959 filed on Dec. 31, 2008, the entire content of which is incorporated by reference herein. Nonlimiting examples of suitable substituted phenylene aromatic diester are provided in Table 1 below.

TABLE 1

| Compound | Structure | $^1$H NMR (500 MHz, CDCl$_3$, ppm) |
|---|---|---|
| 3-methyl-5-tert-butyl-1,2-phenylene dibenzoate | 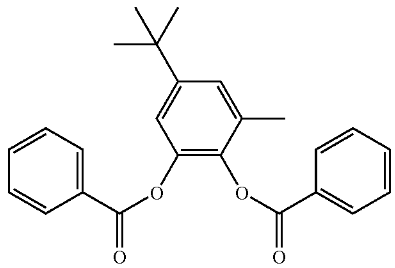 | δ 8.08 (dd, 2H), 8.03 (dd, 2H), 7.53 (tt, 1H), 7.50 (tt, 1H), 7.38 (t, 2H), 7.34 (t, 2H), 7.21 (d, 1H), 7.19 (d, 1H), 2.28 (s, 3H), 1.34 (s, 9H). |
| 3,5-diisopropyl-1,2-phenylene dibenzoate | 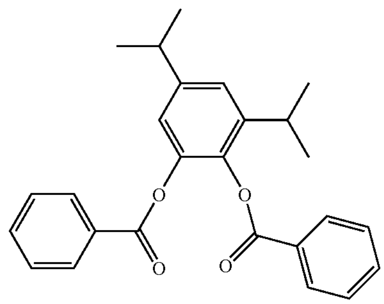 | δ 8.08 (dd, 2H), 7.00 (dd, 2H), 7.53 (tt, 1H), 7.48 (tt, 1H), 7.39 (t, 2H), 7.31 (t, 2H), 7.11 (d, 1H), 7.09 (d, 1H), 3.11 (heptat, 1H), 2.96 (heptat, 1H), 1.30 (d, 6H), 1.26 (d, 6H). |
| 3,6-dimethyl-1,2-phenylene dibenzoate | 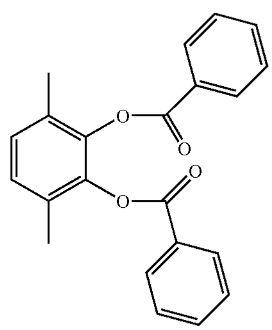 | δ 8.08 (d, 2H), 7.51 (t, 1H), 7.34 (d, 2H), 7.11 (s, 2H), 2.23 (s, 6H). |
| 4-t-butyl-1,2-phenylene dibenzoate | 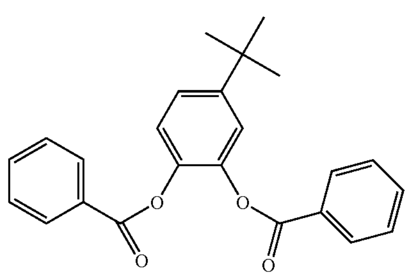 | δ 8.07 (dd, 4H), 7.54 (m, 2H), 7.30-7.40 (m, 7H), 1.37 (s, 9H). |
| 4-methyl 1,2-phenylene dibenzoate | 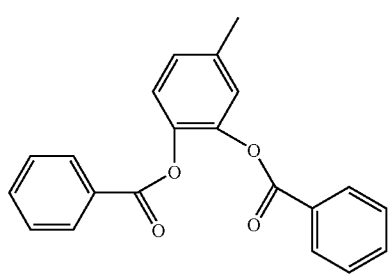 | δ (ppm) 8.07 (d, 4H), 7.54 (t, 2H), 7.37 (t, 4H), 7.27 (d, 1H), 7.21 (s, 1H), 7.15 (d, 1H), 2.42 (s, 3H). |

TABLE 1-continued

| Compound | Structure | $^1$H NMR (500 MHz, CDCl$_3$, ppm) |
| --- | --- | --- |
| 1,2-naphthalene dibenzoate | 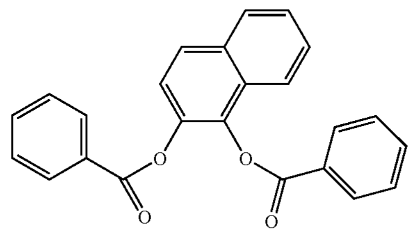 | δ 8.21-8.24 (m, 2H), 8.08-8.12 (m, 2H), 7.90-7.96 (m, 2H), 7.86 (d, 1H), 7.60 (m, 1H), 7.50-7.55 (m, 4H), 7.46 (t, 2H), 7.37 (t, 2H). |
| 2,3-naphthalene dibenzoate | 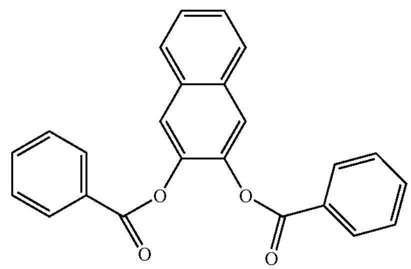 | δ 8.08-8.12 (m, 4H), 7.86-7.90 (m, 4H), 7.51-7.58 (m, 4H), 7.38 (t, 4H) |
| 3-methyl-5-tert-butyl-1,2-phenylene di(4-methylbenzoate) | 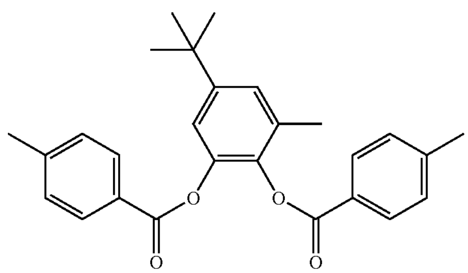 | δ (ppm) 7.98 (d, 2H), 7.93 (d, 2H), 7.18 (d, 4H), 7.15 (d, 2H), 2.38 (s, 3H), 2.36 (s, 3H), 2.26 (s, 3H), 1.35 (s, 9H). |
| 3-methyl-5-tert-butyl-1,2-phenylene di(2,4,6-trimethylbenzoate) | 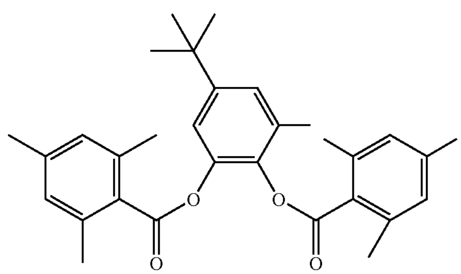 | δ (ppm) 7.25 (s, 1H), 7.21 (s, 1H), 6.81 (d, 4H), 2.36 (s, 3H), 2.30 (d, 6H), 2.25 (s, 6H), 2.23 (s, 6H), 1.36 (s, 9H). |
| 3-methyl-5-tert-butyl-1,2-phenylene di(4-fluorobenzoate) | 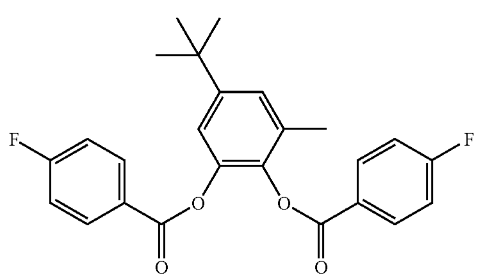 | δ 7.98 (dd, 4H), 7.36 (dd, 4H), 7.21 (s, 1H), 7.17 (s, 1H), 2.26 (s, 3H), 1.34 (s, 9H). |

TABLE 1-continued

| Compound | Structure | $^1$H NMR (500 MHz, CDCl$_3$, ppm) |
|---|---|---|
| 3-methyl-5-tert-butyl-1,2-phenylene di(4-chlorobenzoate) | 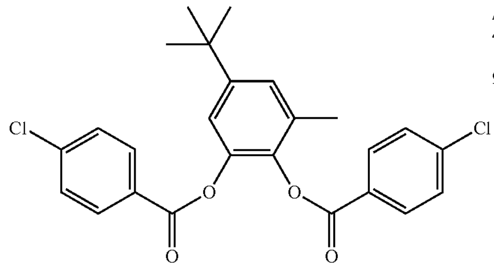 | Δ 7.98 (dd, 4H), 7.36 (dd, 4H), 7.21 (s, 1H), 7.17 (s, 1H), 2.26 (s, 3H), 1.34 (s, 9H). |

2. Procatalyst Compositions

At ambient temperature, 351 g of a mixed magnesium/titanium halide alcoholate is agitated in a mixture of 1.69 kg of chlorobenzene and 4.88 kg of titanium(IV) chloride. After 10 minutes, 750 mL of a chlorobenzene solution containing 164.5 g of 5-tert-butyl-3-methyl-1,2-phenylene dibenzoate is added, followed by an additional 0.46 kg of chlorobenzene. The mixture is agitated at 100° C. for 60 minutes, allowed to settle, then filtered at 100° C. The solids are agitated in 3.16 kg of chlorobenzene at 70° C. for 15 minutes, allowed to settle, then filtered at 70° C. The solids are agitated in a mixture of 2.36 kg of chlorobenzene and 4.84 kg of titanium (IV) chloride, and after 10 minutes, a solution of 109.7 g of 5-tert-butyl-3-methyl-1,2-phenylene dibenzoate in 416 g of chlorobenzene is added, followed by an additional 0.20 kg of chlorobenzene. The mixture is agitated at 105-110° C. for 30 minutes, allowed to settle, then filtered at 105-110° C. The solids are agitated in a mixture of 3.10 kg of chlorobenzene and 4.84 kg of titanium(IV) chloride at 105-110° C. for 30 minutes, allowed to settle, then filtered at 105-110° C. After cooling, the solids are washed twice with 3.47 kg of hexane at 45° C., followed by a final wash with 3.47 kg of 2-methylbutane at ambient temperature. The solids are subjected to vacuum to remove residual volatiles, then combined with 683 g of mineral to generate a slurry.

Comparative Sample 1 (CS1) is a random propylene/ethylene copolymer available from Hyosung Corporation, Korea.

Comparative Sample 2 (CS2) is a random propylene/ethylene copolymer made from SHAC™ 205, a magnesium-containing catalyst (MagMo) with di-isobutyl phthalate as internal electron donor, available commercially from The Dow Chemical Company.

3. Polymerization

Polymerization is performed in a gas phase fluidized bed polymerization reactor (14-inch reactor diameter). The cocatalyst is triethylaluminum, the external electron donor is dicyclopentyldimethoxysilane (DCPDMS), n-propyltrimethoxysilane (NPTMS), or n-propyltriethoxysilane (PTES), and the activity limiting agent is isopropyl myristate (IPM). Specific reactor conditions an resultant polymer properties are provided in Table 3 below.

TABLE 3

Random Propylene/Ethylene Copolymer

| | Example | | | | |
|---|---|---|---|---|---|
| | 1 | 2 | CS1 | 3 | CS2 |
| Catalyst | 1 | 1 | Hyosung R200P Commercial sample | 1 | SHAC 205 |
| MFR (g/10 min) | 0.2 | 0.19 | 0.25 | 127 | 101 |
| Wt. % Et (NMR) | 3.74 | 3.81 | 4.42 | 3.83 | 3.74 |
| XS (wt. %) | 8.6 | 8.2 | 9.5 | 8.7 | 7.8 |
| Melt strength cN, 190° C. | 44 | 40.4 | 36.9 | | |
| 1% SFM (kpsi) | 127 | 121 | 117 | 165.0 | 147.1 |
| RT Izod (ft-lb/in) | 3.18 | 3.57 | 9.98 | | |
| PDI (cone & plate) | 5.09 | 5.01 | 3.82 | 4.54* | 4.03* |
| Tm (° C.) | | | | 144.5 | 145.4 |
| Tm2 (° C.) | | | | 133.9 | 135.6 |
| Tc (° C.) | | | | 118.3 | 116.8 |
| ΔHf (J/g) | | | | 91.6 | 90.8 |
| Clarity (%) | | | | 98.04 | 98.1 |
| Haze (%) | | | | 8.3 | 9.5 |
| Gloss (45) | | | | 92.8 | 81.6 |
| Mn | 95,120 | 100,900 | 143,000 | | |
| Mw | 871,000 | 820,000 | 723,300 | | |
| Mz | 4,482,000 | 3,748,000 | 2,909,000 | | |
| Mw/Mn | 9.16 | 8.13 | 5.06 | | |
| Mz/Mw | 5.15 | 4.57 | 4.02 | | |
| Triad Distribution | | | | | |
| EEE | 0.0034 | 0.0034 | 0.0076 | 0.0025 | 0.0037 |
| EEP | 0.0047 | 0.0048 | 0.0076 | 0.0042 | 0.0050 |
| PPE | 0.0426 | 0.0437 | 0.0421 | 0.0445 | 0.0404 |
| PEP | 0.0423 | 0.0432 | 0.0421 | 0.0455 | 0.0414 |

TABLE 3-continued

Random Propylene/Ethylene Copolymer

| | Example | | | | |
|---|---|---|---|---|---|
| | 1 | 2 | CS1 | 3 | CS2 |
| PPP | 0.8553 | 0.8521 | 0.8433 | 0.8493 | 0.8581 |
| PEE | 0.0047 | 0.0048 | 0.0076 | 0.0042 | 0.0050 |
| EPP | 0.0426 | 0.0437 | 0.0421 | 0.0445 | 0.0404 |
| EPE | 0.0044 | 0.0043 | 0.0076 | 0.0052 | 0.0060 |
| le | | | | 1.13 | 1.19 |
| lp | | | | 18.97 | 20.37 |
| Koenig B-value | 0.9 | 0.92 | 0.82 | 0.93 | 0.89 |
| Polypropylene triad tacticity | | | | | |
| mm % | 96.66 | 97.2 | 95.8 | 98.36 | 97.24 |
| mr % | 0.75 | 0.48 | 1.24 | 0.59 | 1.52 |
| rr % | 2.59 | 2.3 | 2.93 | 1.04 | 1.24 |
| $C_{12}$ | | | | 115 | 120 |
| $C_{15}$ | | | | 177 | 285 |
| $C_{18}$ | | | | 206 | 172 |
| $C_{21}$ | | | | 235 | 388 |
| total (ppmw) | | | | 733 | 965 |

*PDI determined by ModSep

CS2 and Example 3 each contain the additive package shown in Table 4.

TABLE 4

| Additives (ppm) | | |
|---|---|---|
| Irganox 1010 | 500 | 500 |
| Irgafos 168 | 1000 | 1000 |
| CaSt | 500 | 500 |
| DHT-4A | 150 | 150 |
| Uvitex OB | 10 | 10 |
| Millad 3988i | 2000 | 2000 |
| GMS 90 | 1000 | 1000 |

It is specifically intended that the present disclosure not be limited to the embodiments and illustrations contained herein, but include modified forms of those embodiments including portions of the embodiments and combinations of elements of different embodiments as come within the scope of the following claims.

The invention claimed is:

1. A polymerization process comprising:
   contacting, under polymerization conditions, propylene and ethylene with a catalyst composition comprising a substituted phenylene aromatic diester; and
   forming a random propylene/ethylene copolymer with a Koening B-value from greater than or equal to 0.83 to about 1.0.

2. The polymerization process of claim 1 comprising maintaining a $H_2/C_3$ molar ratio from 0.002 to 0.02 and forming a propylene/ethylene copolymer having a melt flow rate from 0.1g/10 min to 5 g/10 min as measured in accordance with ASTM D 1238, 2.16 kg, 230° C.

3. The polymerization process of claim 1 comprising maintaining a $H_2/C_3$ molar ratio from 0.010 to 0.25 and forming a propylene/ethylene copolymer having a melt flow rate from greater than 5 g/10 min to about 800 g/10 min as measured in accordance with ASTM D 1238, 2.16, 230° C.

* * * * *